United States Patent
Ikuta et al.

(10) Patent No.: US 10,894,067 B2
(45) Date of Patent: Jan. 19, 2021

(54) GENOME STABILITY ENHANCER

(71) Applicants: Yamada Bee Company, Inc., Okayama (JP); National Cancer Center, Tokyo (JP); Tohoku University, Miyagi (JP)

(72) Inventors: Tomoki Ikuta, Okayama (JP); Shinobu Fukushima, Okayama (JP); Tomoki Tatefuji, Okayama (JP); Kenichi Yoshioka, Tokyo (JP); Hitoshi Shirakawa, Miyagi (JP)

(73) Assignees: Yamada Bee Company, Inc., Okayama (JP); National Cancer Center, Tokyo (JP); Tohoku University, Miyagi (JP)

( * ) Notice: Subject to any disclaimer, the term of this patent is extended or adjusted under 35 U.S.C. 154(b) by 0 days.

(21) Appl. No.: 16/494,009

(22) PCT Filed: Mar. 6, 2018

(86) PCT No.: PCT/JP2018/008606
§ 371 (c)(1),
(2) Date: Sep. 13, 2019

(87) PCT Pub. No.: WO2018/168579
PCT Pub. Date: Sep. 20, 2018

(65) Prior Publication Data
US 2020/0023017 A1    Jan. 23, 2020

(30) Foreign Application Priority Data

Mar. 16, 2017 (JP) ................. 2017-051280

(51) Int. Cl.
| | |
|---|---|
| *A61K 35/644* | (2015.01) |
| *A23L 33/105* | (2016.01) |
| *A61K 8/9755* | (2017.01) |
| *A61K 8/49* | (2006.01) |
| *A61K 8/98* | (2006.01) |
| *A61K 31/343* | (2006.01) |
| *A61K 36/13* | (2006.01) |

(52) U.S. Cl.
CPC .......... *A61K 35/644* (2013.01); *A23L 33/105* (2016.08); *A61K 8/4973* (2013.01); *A61K 8/9755* (2017.08); *A61K 8/988* (2013.01); *A61K 31/343* (2013.01); *A61K 36/13* (2013.01); *A23V 2002/00* (2013.01)

(58) Field of Classification Search
None
See application file for complete search history.

(56) References Cited

U.S. PATENT DOCUMENTS

2018/0000871 A1* 1/2018 Asama ................. A61K 35/644

FOREIGN PATENT DOCUMENTS

| JP | 2007/295919 A | 11/2007 |
| JP | 2011/079797 A | 4/2011 |
| JP | 5923699 B | 5/2016 |
| JP | 5979810 B | 8/2016 |
| JP | 6082551 | * 2/2017 |

OTHER PUBLICATIONS

Al-Dujaily S. et al. Effect of Royal Jelly on DNA Integrity of Epididymal Sperms in Vasectomized and Non-Vasectomized Mice . . . World J of Pharmaceutical Research 4(6)2343-2351, 2015. (Year: 2015).*
Chen et al "10-Hydroxy-2-Decenoic Acid (10-HAD) Inhibits Peroxynitrite-Mediated DNA Damage and Hydroxyl Radical Formation, Implication for its Cancer Intervention" Free Radical Biology and Medicine vol. 47, p. S160, abstract 436, 2009.
Honda et al "Lifespan-Extending Effects of Royal Jelly and its Related Substances on the Nematode *Caenorhabditis elegans*" PLOS One vol. 6, pp. 1-10, 2011.
Hsieh et al "Control of Prostate Cell Growth, DNA Damage and Repair and Gene Expression by Resveratrol Analogues, In Vitro" Carcinogenesis vol. 32, pp. 93-101, 2011.
Ikuta et al "Resveratrol Derivative-Rich Melinjo (*Gnetum gnemon* L.) Seed Extract Improves Obesity and Survival of C57BL/6 Mice Fed a High-Fat Diet" Bioscience, Biotechnology, and Biochemistry vol. 79, pp. 2044-2049, 2015.
Narayanan et al "Antitumor Activity of Melinjo (*Gnetum gnemon* L.) Seed Extract in Human and Murine Tumor Models In Vitro and in a Colon-26 Tumor-Bearing Mouse Model In Vivo" Cancer Medicine vol. 4, pp. 1767-1780, 2015.
Podhorecka et al "Resveratrol Increases Rate of Apoptosis Caused by Purine Analogues in Malignant Lymphocytes of Chronic Lymphocytic Leukemia" Annals of Hematology vol. 90, pp. 173-183, 2011.
Tamura et al "Antitumor Effects of Royal Jelly" Folia Pharmacologica Japonica vol. 89, pp. 73-80, 1987.
Yoshioka "Study on Molecular Mechanism of Genome Instability/Mutation/Cell Transformation Which Originates From, and is Induced According to Cancer-Inducing Stress" 23-C-10, pp. 1-5, 2015.
Yoshioka et al "Study on Canceration and Aging Prevention Effects Using Nutrition Components, and Genome Stability Control Mechanism" Mishima Kaiun Memorial Foundation Research Report No. 53, pp. 18-21, 2016.

* cited by examiner

*Primary Examiner* — Ralph J Gitomer
(74) *Attorney, Agent, or Firm* — Cesari and McKenna, LLP (57) ABSTRACT

Disclosed is a genome stability enhancer comprising, as an active ingredient, at least one member selected from the group consisting of enzyme-treated royal jelly, gnetum or its extract, and gnetin C.

8 Claims, 3 Drawing Sheets

Melinjo Seed Extract

GENOME STABILITY ENHANCER

CROSS-REFERENCE TO RELATED APPLICATIONS

This application is the National Stage of International Application No. PCT/JP2018/008606, filed Mar. 6, 2018, which claims the benefit of priority of Japanese Patent Application No. 2017-051,280, filed Mar. 16, 2017, the contents of both being incorporated by reference in their entirety for all purposes.

TECHNICAL FIELD

The present invention relates to a genome stability enhancer.

BACKGROUND ART

Most normal cells stop their proliferation after predetermined cycles of cell division. Static cells are protected from transformation as long as the genome stability is maintained. This static state is formed in line with decreased histone H2AX levels under the regulation of ARF/p53 pathway. Such an arrest of proliferation is also widely observed in cells that form organs that normally maintain homeostasis. When H2AX levels are lowered, cells stop growing, and the DNA damage repair capacity simultaneously decreases. Thus, genome instability is induced in cells that have stopped growing, accompanied by DNA replication stress caused by excessive growth stimuli Such cells, however, have a repair capacity activation mechanism associated with transient H2AX induction.

Histone H2AX plays an important role in localization of DNA damage repair factors in a damaged site. When a DNA double-strand break occurs, H2AX around the break is phosphorylated. Many DNA damage repair factors interact with this phosphorylated H2AX (called "γ-H2AX") and are thereby localized in the damaged site. Thus, γ-H2AX is usable as a marker for DNA damage, for example, by detecting it by immunostaining.

In order to examine the efficacy of resveratrols on cancer cells, NPL 1 and 2, for example, confirmed by detecting γ-H2AX that resveratrols induce DNA damage. The DNA damage in cancer cells then leads to an apoptosis-inducing effect.

As noted above, NPL 1 and 2 disclose detection of phosphorylated H2AX, but include no study into the expression level of H2AX itself. As stated above, transiently inducing H2AX activates the DNA repair capacity, and this improves genome stability.

NPL 3 reports that DNA repair associated with transient H2AX expression in normal cells that have stopped growing was discovered in treatment with resveratrol and royal jelly.

NPL 4 reports that factor X involved in DNA repair is transiently induced by resveratrol. Some literature also reports that royal jelly and melinjo rich in resveratrol derivatives also have anticancer action, anti-aging action, a life extension effect, etc. (PTL 1 and 2, and NPL 5 to 8).

However, effective treatments have yet to be found for diseases caused by mutation in the gene repair mechanism, such as xeroderma pigmentosum, Huntington's disease, Werner's syndrome, Bloom's syndrome, and Lynch syndrome.

CITATION LIST

Patent Literature

PTL 1: Japanese Patent No. 5923699
PTL 2: Japanese Patent No. 5979810

Non-Patent Literature

NPL 1: Carsinogenesis (2011) 32(1): 93-101
NPL 2: Ann Hematol (2011) 90: 173-183
NPL 3: Kenichi Yoshioka, 23-C-10, Study on molecular mechanism of "genome instability/mutation/cell transformation" which originates from, and is induced according to cancer-inducing stress <http://crdb.ncc.go.jp/search/DRTV050.action?rpno=012013007100000>
NPL 4: Kenichi Yoshioka, Hitoshi Shirakawa, Study on canceration and aging prevention effects using nutrition components, and genome stability control mechanism <http://www.mishima-kaiun.or.jp/assist/docs/SJNo2-yoshioka.pdf>
NPL 5: Folia pharmacol Japon (1987) 89:73-80
NPL 6: Cancer Medicine (2015) 4(11):1767-1780
NPL 7: PLoS One (2011) 6(8): e23527
NPL 8: Bioscience, Biotechnology, and Biochemistry (2015) 79(12): 2044-2049

SUMMARY OF INVENTION

Technical Problem

An object of the present invention is to provide a genome stability enhancer having an excellent genome stability enhancement effect.

Solution to Problem

As a result of extensive research to achieve the above object, the present inventors found that enzyme-treated royal jelly has a higher H2AX-inducing effect than non-enzyme-treated royal jelly, and that a melinjo seed extract and gnetin C have a higher H2AX-inducing effect than trans-resveratrol.

Based on the above findings, the inventors conducted further research and accomplished the present invention. The present invention provides a genome stability enhancer described below.

Item 1. A genome stability enhancer comprising, as an active ingredient, at least one member selected from the group consisting of enzyme-treated royal jelly, gnetum or its extract, and gnetin C.

Item 2. The genome stability enhancer according to Item 1, which is a cosmetic, food or beverage, drug, or quasi-drug.

Item 3. A method for enhancing genome stability, comprising the step of administering an effective amount of at least one member selected from the group consisting of enzyme-treated royal jelly, gnetum or its extract, and gnetin C to a mammal.

Item 4. Use of at least one member selected from the group consisting of enzyme-treated royal jelly, gnetum or its extract, and gnetin C, for producing a genome stability enhancer.

Item 5. The use according to Item 4, wherein the genome stability enhancer is a cosmetic, food or beverage, drug, or quasi-drug.

Item 6. A composition for use in enhancement of genome stability comprising, as an active ingredient, at least one member selected from the group consisting of enzyme-treated royal jelly, gnetum or its extract, and gnetin C.

Item 7. The composition for use in enhancement of genome stability according to Item 6, which is a cosmetic, food or beverage, drug, or quasi-drug.

Advantageous Effects of Invention

Since enzyme-treated royal jelly, gnetum or its extract, and gnetin C have an excellent H2AX expression-inducing effect, they are effective as active ingredients of a genome stability enhancer.

Since the genome stability enhancer of the present invention has an excellent genome stability enhancement effect, it is expected to have an effect of preventing development of, and alleviating symptoms of, diseases relating to genome instability (abnormality in gene repair mechanism), such as xeroderma pigmentosum, Huntington's disease, Werner's syndrome, Bloom's syndrome, and Lynch syndrome.

DESCRIPTION OF EMBODIMENTS

The present invention is explained in detail below.

In this specification, the terms "contain" and "comprise" encompass the meanings of "essentially consist of" and "consist of."

The genome stability enhancer of the present invention comprises, as an active ingredient, at least one member selected from the group consisting of enzyme-treated royal jelly, gnetum or its extract, and gnetin C.

Royal jelly is a milky jelly-like material formed by mixing secretion secreted from the hypopharyngeal and mandibular glands of 3- to 12-day-old worker bees among honey bees. Examples of the main bioactive components in royal jelly include organic acids, such as 10-hydroxy decenoic acid (hereinbelow referred to as "decenoic acid") that is specific to royal jelly; proteins; lipids; saccharides; vitamins, such as vitamin B, folic acid, nicotinic acid, and pantothenic acid; various minerals; and the like. Known bioactive and pharmacological effects of royal jelly include antimicrobial effects, immune-enhancing effects, antidepressant effects, antitumor effects, anti-inflammatory effects, blood flow increase effects, and the like. Additionally, reduction in side effects of anticancer drugs, and effects of extending life in radiation damage have also been reported.

Royal jelly used in the production of enzyme-treated royal jelly is not particularly limited. Usable examples include raw royal jelly, royal jelly powder obtained by drying and powderizing raw royal jelly, or an extract obtained by extracting raw royal jelly using water, water-containing ethanol, and the like.

The production areas of royal jelly are not limited, and examples include Japan, China, Brazil, European countries, Oceania countries, the United States, and the like.

The enzyme-treated royal jelly of the present invention is a product formed by treating royal jelly with a protease. Preferred is enzyme-treated royal jelly having reduced allergenicity in which allergic reaction due to the protein in the royal jelly is suppressed by a peptidase treatment. Accordingly, the enzyme-treated royal jelly of the present invention includes, in addition to a peptidase-degraded product of protein contained in the royal jelly, decenoic acid and like organic acids as mentioned above, lipids, saccharides, vitamins, and various minerals.

A preferable enzyme used for enzyme-treating royal jelly may be a peptidase. The peptidase to be used only needs to have at least one of endopeptidase action or exopeptidase action. A peptidase having at least endopeptidase action is preferred, and a peptidase having both actions is more preferred.

The enzyme-treated royal jelly of the present invention is preferably obtained by subjecting protein contained in royal jelly to hydrolyzation to thereby reduce allergenicity. To obtain such enzyme-treated royal jelly, it is preferable to hydrolyze royal jelly by using a peptidase (endopeptidase) having at least endopeptidase action, and preferably using a peptidase having both endopeptidase action and exopeptidase action. As a peptidase having both endopeptidase action and exopeptidase action, a peptidase simultaneously having both actions can be used singly, or a peptidase (endopeptidase) having endopeptidase action and a peptidase (exopeptidase) having exopeptidase action can be used in combination.

In the present invention, any endopeptidase can be used as long as it is a protease having at least endopeptidase activity. For example, various endopeptidases derived from animals (e.g., trypsin and chymotrypsin), endopeptidases derived from plants (e.g., papain), and endopeptidases derived from microorganisms (e.g., *lactobacilli*, yeast, fungi, *Bacillus subtilis*, and actinomycetes) can be used.

Any exopeptidase can be used as long as it is a protease having at least exopeptidase activity. Examples include carboxypeptidase, aminopeptidase, and exopeptidases derived from microorganisms (e.g., *lactobacilli*, fungi of the genus *Aspergillus*, and fungi of the genus *Rhizopus*). Pancreatin and pepsin, each of which also has endopeptidase activity, can also be used.

Peptidases include exopeptidases substantially having exopeptidase action alone, endopeptidases substantially having endopeptidase action alone, and peptidases having both exopeptidase action and endopeptidase action. Of these, enzymes having both exopeptidase action and endopeptidase action can be used as endopeptidases when the endopeptidase action is strong, can be used as exopeptidases when the exopeptidase action is strong, and can be used as peptidases simultaneously having exopeptidase action and endopeptidase action when the endopeptidase action is equal to, or substantially equal to, the exopeptidase action.

Of such peptidases, preferred examples of the enzyme having exopeptidase action include a peptidase produced with *Aspergillus oryzae* (product name: Umamizyme G, Promod 192P, Promod 194P, and Sumizyme FLAP), a peptidase produced with *Aspergillus sojae* (product name: Sternzyme B15024), a peptidase produced with the genus *Aspergillus* (product name: Kokulase P), and a peptidase produced with *Rhizopus oryzae* (product name: Peptidase R).

Preferred examples of the peptidase having endopeptidase action include a peptidase produced with *Bacillus subtilis* (product names: Orientase 22BF and Nucleicin), a peptidase produced with *Bacillus licheniformis* (product name: ALCALASE), a peptidase produced with *Bacillus stearothermophilus* (product name: Protease S), a peptidase produced with *Bacillus amyloliquefaciens* (product name: Neutrase), and a peptidase produced with the genus *Bacillus* (product name: Prometax).

Further, preferred examples of the peptidase having both exopeptidase action and endopeptidase action, particularly preferred examples of alkaline peptidases, include a peptidase produced with *Streptomyces griseus* (product name: Actinase AS), a peptidase produced with *Aspergillus oryzae* (product names: Protease A and Flavourzyme), and a peptidase produced with *Aspergillus melleus* (product name: Protease P). Since an enzyme treatment using such a peptidase allows protein to be broken into a lower molecular compound by one-step enzyme treatment, the operation is simple, and it is possible to prevent loss and significant reduction in the bioactivity of effective components contained in the royal jelly.

The amount of peptidase relative to royal jelly varies depending on the concentration of the royal jelly to be used, enzymatic activity value, reaction temperature, and reaction time. In general, it is preferable to use the peptidase in a proportion of 50 to 10000 unit per gram of protein in royal jelly. In this case, the peptidase may be added to the royal jelly at once, or gradually and separately.

The pH of the royal jelly in the peptidase treatment can be selected from a pH range of 2 to 12, preferably a pH range of 7.5 to 10, and more preferably a pH range of 7.8 to 9 according to the suitable pH range of the enzyme to be used. Specifically, before the peptidase is added to the royal jelly, depending on the kind of the enzyme to be used, the pH of the royal jelly is adjusted to a desired range, i.e., a pH of 2 to 12, preferably a pH of 7.5 to 10, and more preferably a pH of 7.8 to 9, by adding an acid, alkali agent, or buffer. In this case, examples of acids include hydrochloric acid, sulfuric acid, nitric acid, phosphoric acid, acetic acid, and the like; examples of alkaline agents include sodium hydroxide, potassium hydroxide, potassium carbonate, and the like; and examples of buffers include phosphoric acid buffers, citric acid buffers, and the like.

The temperature of the peptidase treatment is not particularly limited. The temperature may be generally selected from the range of practical use including an optical temperature range at which peptidase action, preferably endopeptidase action, and more preferably both endopeptidase action and exopeptidase action are exhibited, i.e., the range between 30 and 70° C. By maintaining the temperature to a temperature lower or higher than the optimum peptidase temperature (preferably about 40 to 50° C.), e.g., the range between 50 and 60° C., decomposition in the step of peptidase treatment can be avoided. The time for the peptidase treatment depends on the kind of the enzyme to be used and reaction conditions, such as reaction temperature and pH, and is not particularly limited.

The royal jelly can be subjected to a protease treatment without any treatment or after being dissolved or dispersed in water. If the royal jelly is in a dried form, it is preferably subjected to a protease treatment after being dissolved in water.

The peptidase treatment stops by deactivating or removing peptidase. Deactivation operation can be conducted by using a heating treatment (e.g., at 85° C. for 15 minutes.)

As described above, the enzyme-treated royal jelly of the present invention may be royal jelly that is treated with at least a peptidase. The enzyme-treated royal jelly of the present invention also includes royal jelly that is treated with a combination of a peptidase and other enzyme(s), e.g., a peptidase and a glycolytic enzyme.

As the enzyme-treated royal jelly of the present invention, royal jelly that is dried and powderized after being enzyme-treated can be used. As a drying method, known methods used for general food processing can be used. Examples include natural drying, such as draught drying and solar drying, forced drying in which royal jelly is dried by heating using electricity, fluidized bed drying, spray drying, high-frequency drying, and freeze drying. Of these, freeze drying is preferred. As a pulverization method for powderizing royal jelly, known methods, such as pulverization methods using a grinding mill (e.g., pin mill, hammer mill, ball mill, jet mill, roller mill, and colloid mill) can be used.

Gnetum (synonym: Melinjo, scientific name: *Gnetum gnemon* L, English name: Gnemon tree, Indonesian name: Melinjo, Belinjo) is a Gnetaceae plant and is grown in Southeast Asia.

Parts of gnetum used in the present invention are not particularly limited. Examples include fruits (or seeds), flowers, leaves, and the like, and preferably seeds. Processed gnetum can be also used. Examples of processing include drying, heat drying, cutting, pulverizing, etc.

In this specification, a gnetum seed consists of a episperm, pellicle, and embryo/albumen (endosperm). As long as the effect of the present invention can be attained, the gnetum seed can be in any shape and form. Preferred is a peanut-like seed having a long diameter of about 1.3 to 2.3 cm and a short diameter of about 0.6 to 1.3 cm. A product containing a gnetum seed can be used in the present invention. Examples include a gnetum fruit in which a gnetum seed has a pericarp.

Examples of the gnetum seed used in the present invention also include processed products. Examples of the processed product of the gnetum seed include dried products (i.e., sun-dried), heat-dried products, and the like. As the gnetum seed, gnetum seeds that maintain the original shape, i.e., those that are not cut or pulverized, and processed products of sliced or pulverized gnetum seeds can be used. In the present invention, a processed product of a gnetum seed having an embryo/albumen (endosperm) alone or an episperm alone can be also used.

In the present invention, it is desirable to use an extract of a gnetum seed. The method for producing such an extract is not particularly limited, and examples include an extraction method in which a gnetum seed is immersed in an immersion fluid (the method described in JP2013-82701A).

As the above immersion fluid, water, an organic solvent, or a water-containing organic solvent can be used. An organic solvent that can be freely mixed with water is preferred. Examples include $C_{1\text{-}5}$ lower alcohols, such as methanol, ethanol, 1-propanol, 2-propanol, 1-butanol, 2-butanol, 2-methyl-1-propanol, 2-methyl-2-propanol, 1-pentanol, 2-pentanol, and 3-pentanol; ethers, such as diethylether; esters, such as methyl acetate and ethyl acetate; ketones, such as acetone; organic acids, such as acetic acid, glacial acetic acid, and propionic acid; and the like. The organic solvent is preferably a lower alcohol.

The temperature of the immersion fluid used in immersion can be suitably determined according to the amounts of the gnetum seed and immersion fluid, and is, for example, 10 to 50° C., and preferably 20 to 40° C. The time for immersion can be suitably determined according to the amounts of the gnetum seed and immersion fluid, and is preferably 3 days or more, and more preferably 3 to 7 days.

The collected immersion fluid can be used as is, or can be purified by ultrafiltration, molecular sieve chromatography (gel filtration), adsorption chromatography, ion exchange chromatography, affinity chromatography, high-performance liquid chromatography (HPLC), dialysis, or a combination thereof, if necessary.

The extract of the gnetum seed can take any form, such as a collected immersion fluid (optionally including a further purified product), concentrated fluid in which the immersion fluid is concentrated, or solid in which a solvent of the immersion fluid is removed by freeze-drying, spray-drying, or the like. Concentration, freeze-drying, and spray-drying of the immersion fluid can be performed according to a conventional method. The form of the extract of the gnetum seed according to the present invention is preferably a powder.

Gnetin C is a type of polyphenol shown in the following formula.

As gnetin C, a product prepared in-house or a commercially available product can be both used. The method for preparing gnetin C in-house is not particularly limited. Examples include a method for extracting gnetin C from a plant containing gnetin C, a method for producing gnetin C by a microorganism (for example, see Adil E. Bala et al., "Antifungal activity of resveratrol oligomers from Cyphostemma crotalarioides," Pesticide Science, Vol. 55, Issue 2, pages 206-208), and a method for chemically synthesizing gnetin C.

Plants containing gnetin C are not particularly limited. Preferred are plants belonging to the family Gnetaceae (Ibrahim Iliya et al., "Stilbenoids from the stem of Gnetum latifolium (Gnetaceae)," Phytochemistry, 2002 December; 61(8): 959-61; Ibrahim Iliya et al., "Dimeric Stilbenes from Stem Lianas of Gnetum Africanum," HeteroCycles, Vol. 57, No. 6, pages 1057-1062 (2002)).

Specific examples include *Gnetum latifolium*, *Gnetum Africanum*, and *Gnetum gnemon* (gnetum), each belonging to the family Gnetaceae, and gnetum is preferred. Parts of plants to be used are not limited as long as the parts include gnetin C in a large amount. Fruits (or seeds), flowers, leaves, and other parts can be used without limitation, and fruits (or seeds) are preferred, and albumen of fruits are more preferred.

Methods for extracting gnetin C from plants are not particularly limited. The extraction methods described above and the extraction method described in JP2013-82701A can be used. As gnetin C, products (crude extracts) that are not isolated or purified, and products that are isolated or purified, can be both used. As a purification method, those as described above can be used.

There is no need to perform purification until the purity is 100%. Gnetin C used in the present invention generally has a purity of 50 mass % or more, preferably 80 mass % or more, and more preferably 90 mass % or more.

To produce gnetin C using a microorganism, or to obtain gnetin C by chemical synthesis, it is preferable to perform a purification treatment as mentioned above.

Gnetin C in the present invention may be in a free form or salt form. Examples of salts include salts with inorganic bases, such as sodium salt, potassium salt, magnesium salt, calcium salt, and aluminum salt; salts with organic bases, such as methylamine, ethylamine, and ethanolamine; salts with basic amino acids, such as lysine, ornithine, and arginine; and ammonium salts. The salts may be acid-added salts, and examples include acid-added salts with mineral acids, such as hydrochloric acid, hydrobromic acid, hydroiodic acid, sulfuric acid, nitric acid, and phosphoric acid; acid-added salts with organic acids, such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; and acid-added salts with acidic amino acids, such as aspartic acid and glutamic acid. Gnetin C in the present invention also includes hydrates, solvates, crystal polymorphisms, and the like of gnetin C.

The amount of enzymatically treated royal jelly in the genome stability enhancer of the present invention is not particularly limited. It is preferably 0.01 mass % or w/v % or more, more preferably 1.4 to 100 mass % or w/v %, and even more preferably 30 to 65 mass % or w/v %.

The amount of gnetum or its extract in the genome stability enhancer of the present invention is not particularly limited, and is preferably 0.01 mass % or w/v % or more, more preferably 0.03 to 100 mass % or w/v %, and even more preferably 30 to 65 mass % or w/v %.

The amount of gnetin C in the genome stability enhancer of the present invention is not particularly limited, and is preferably 0.001 mass % or w/v % or more, more preferably 0.01 to 100 mass % or w/v %, and even more preferably 1 to 40 mass % or w/v %.

The genome stability enhancer of the present invention includes the meanings of cosmetics, foods or beverages (in particular, foods or beverages having the goal of maintaining or promoting health (e.g., health food, functional food, nutritional compositions, dietary supplement food, supplements, food for health uses, food for specified health uses, food with nutrient function claims, and food with function claims)), quasi-drugs, and drugs (in particular, orally administered drugs). The genome stability enhancer of the present invention also includes the meaning of an additive that imparts genome stability enhancement effects.

The cosmetics may optionally contain, in addition to the above active ingredients, ingredients commonly used in cosmetics, such as skin-lightening agents, moisturizers, antioxidants, oily components, ultraviolet absorbers, surfactants, thickeners, alcohols, powder constituents, color materials, aqueous ingredients, water, various skin nutrients, etc.

The cosmetic includes all cosmetics that are applied to the skin, mucosa, body hair, head hair, scalp, nails, teeth, facial skin, lips, etc. of animals (including humans).

The cosmetic can be formulated into a wide range of dosage forms, such as aqueous solutions, solubilizers, emulsions, powders, oils, gels, ointments, aerosols, water-oil bilayer preparations, and water-oil-powder trilayer preparations.

The cosmetic may be used for any purpose of use. Examples of such uses include basic cosmetics, such as facial washes, face lotions, milky lotions, creams, gels, essences, beauty essences, packs, and masks; make-up products, such as foundation, lipstick, blush, eye shadow, eyeliner, and mascara; nail cosmetics, such as nail polish, base coat, topcoat, and nail polish remover; and other products, such as facial washes, dentifrices (paste or liquid), mouthwash, massaging agents, cleansing agents, after-shave lotion, pre-shave lotion, shaving cream, body soap, soap, shampoo, rinse, hair treatment, hair dressings, hair tonic, hair growth agents, antiperspirant, and bath agents.

The foods or beverages may optionally contain, in addition to the above active ingredients, excipients, gloss agents, minerals, vitamins, flavonoids, quinones, polyphenols, amino acids, nucleic acids, essential fatty acids, fresheners, binders, sweeteners, disintegrators, lubricants, coloring agents, fragrances, stabilizing agents, preservatives, sustained-release regulators, surfactants, solubilizers, wetting agents, and the like.

Examples of foods or beverages include those ingestible by animals (including humans) The type of foods or beverages is not limited, and includes drinks (coffee, juice, tea drinks, and like soft drinks; milk beverages; lactic acid bacteria beverages; yogurt beverages; carbonated beverages; sake, liquor, fruit wine, and like alcohol; etc.); spreads (custard cream etc.); pastes (fruit pastes etc.); Western-style confectionery (chocolates, doughnuts, pies, choux, gum, jelly, candies, cookies, cakes, pudding, etc.); Japanese-style confectionery (daifuku (soft round rice cake stuffed with sweet bean jam), mochi (rice cake), manju (steamed azuki bean jam-filled bun), kasutera (Castella cakes), anmitsu (agar jelly served with red bean paste and brown sugar syrup), youkan (sweet jellied adzuki-bean paste), etc.); frozen desserts (ice cream, ice candy, sherbet, etc.); food (curry, beef bowl, porridge of rice and vegetables, miso soup, soup, meat sauce, pasta, pickles, jam, etc.); and seasonings (dressing, furikake (dried food sprinkled over rice), flavor enhancers, soup base, etc.).

The unit dosage form used as a supplement is not limited and can be suitably selected. Examples include tablets (e.g., uncoated tablets, sugar-coated tablets, film-coated tablets, chewable tablets, and troches), capsules, granules, solutions, powders, syrup, pastes, drinks, etc.

The intake amount of the food or beverage can be suitably selected according to the body weight, age, gender, symptoms, and various other conditions of the person taking the food or beverage.

In the drugs, the active ingredient may be used alone, or as a mixture with other pharmaceutical ingredients described in the Japanese Pharmacopoeia, such as vitamins and crude drugs.

To prepare the genome stability enhancer as a drug, the active ingredients may be mixed with a pharmaceutically acceptable non-toxic carrier, diluent, or excipient, and formed into tablets (including uncoated tablets, sugar-coated tablets, effervescent tablets, film-coated tablets, chewable tablets, troches, etc.), capsules, pills, powder (powdered drugs), fine granules, granules, liquids, suspensions, emulsions, syrups, pastes, etc. to form oral formulations.

The dose of the drug can be suitably determined according to various conditions, such as the patient's body weight, age, gender, and symptoms.

The drugs and cosmetics of the present invention include quasi-drugs.

The genome stability enhancer of the present invention explained above is applied to mammals including humans.

As shown in the Examples described later, enzyme-treated royal jelly, gnetum or its extract, and gnetin C, which are all contained as active ingredients in the genome stability enhancer of the present invention, have a higher H2AX-inducing effect than non-enzyme-treated royal jelly and trans-resveratrol. Thus, since the genome stability enhancer of the present invention has an excellent H2AX expression-inducing effect, it is expected to have an excellent genome stability enhancement effect.

Since the genome stability enhancer of the present invention has an excellent genome stability enhancement effect, it is suitably used for preventing development of, alleviating symptoms of, and treating diseases relating to genome instability (abnormality in gene repair mechanism), such as xeroderma pigmentosum, Huntington's disease, Werner's syndrome, Bloom's syndrome, and Lynch syndrome (hereditary nonpolyposis colorectal cancer).

EXAMPLES

The following describes the present invention in more detail with reference to Examples. However, the present invention is not limited to the Examples.

Materials

An enzyme-treated product of royal jelly was prepared in accordance with Example 1 disclosed in the publication of Japanese Patent No. 3994120. The freeze-dried powder of enzyme-treated royal jelly or royal jelly was dissolved in a 10% FBS-added α-MEM medium such that the final concentration was 100 µg/mL, and then the solution was subjected to filter sterilization.

A melinjo seed extract was prepared in accordance with paragraph [0024] of JP2009-013123A. A crushed dry fruit of melinjo was immersed in a water-containing ethanol at room temperature, and the obtained extract was concentrated under reduced pressure, thereby preparing a melinjo seed extract with a solids content of 63.2 mass %.

For gnetin C, 2.5 g of the obtained melinjo seed extract was subjected to column chromatography (type of gel: Cosmosil 75C18-PREP (manufactured by Nacalai Tesque Inc.), column size: 3 dia.×26.5 cm), and stepwise elution was performed using water-containing methanol sequentially with a methanol content of 10 volume %, 25 volume %, 40 volume %, 80 volume %, and 100 volume % as an eluent (600 mL of each eluent was allowed to flow, and 100 mL of each eluent was separated). Each obtained component was studied by HPLC under the following conditions, and gnetin C was confirmed to have been eluted in a retention time of 33.5 minutes (an eluted fraction of water-containing methanol that contained 1 volume % acetic acid and 80 volume % methanol).

HPLC Conditions

Column: manufactured by Tosoh Corporation, TSKgel ODS-100V, 5 µm, 4.6×150 mm

Mobile Phase:
Solution A: 1.0 volume % acetic acid-containing water
Solution B: 1.0 volume % acetic acid-containing methanol
Gradient Conditions: 0 minutes→10 minutes: A:B=65:35 (v/v)→63:37(v/v), 10 minutes→20 minutes: A:B=63:37(v/v)→56:44 (v/v), 20 minutes→40 minutes: A:B=48:52 (v/v)
Detection Wavelength: 320 nm
Flow Rate: 0.8 mL/min The fractions were concentrated and then sequentially eluted by medium-pressure column chromatography under the following conditions.

Conditions for Medium-Pressure Column Chromatography
Type of Gel: Silica Gel, Daisogel IR-60-40/63-W
Column Size: 2 dia.×7.48 cm
Detection Wavelength: 320 nm
Mobile Phase: Solution A (methanol), Solution B (chloroform)
Gradient Conditions: 0 minutes→2 minutes: A:B=11:89 (v/v), 2 minutes→8 minutes: A:B=11:89 (v/v)→18:82 (v/v), 8 minutes→12 minutes: A:B=18:82 (v/v), 12 minutes→14 minutes: A:B=21:79 (v/v), 14 minutes→20 minutes: A:B=21:79 (v/v)→29:71 (v/v), 20 minutes→24 minutes: A:B=29:71 (v/v), 24 minutes→30 minutes: A:B=29:71 (v/v)→36:64 (v/v), 30 minutes→34 minutes: 36:64(v/v)
Flow Rate: 60 ml/min 60 mL of each eluate was separated, and a fraction at segment 29 to segment 30 that exhibited an absorption peak at a detection wavelength of 320 nm was concentrated with an evaporator, thereby obtaining gnetin C (35.2 mg, purity: 97%).

Trans-resveratrol was obtained from Sigma-Aldrich Co. LLC.

Test Example 1

Because growth arrest of normal cells is induced in line with decreased levels of H2AX (which is essential for inducing the accumulation of DNA damage repair factors in a DNA damage site), the DNA repair capacity also simultaneously deceases. It is now clear that genome instability is induced by growth stimulation due to this background. Thus, the effects of enzyme-treated royal jelly (enzyme-treated RJ) and royal jelly (non-treated RJ) on H2AX expression were analyzed.

MEF (mouse embryo fibroblast) cells were cultured at 37° C. in 5% $CO_2$ by the 3T3 method in a 10% FCS (fetal calf serum)-containing DMEM medium to which a 25 μg/ml enzymatically treated RJ or non-treated RJ was added. The cells that were cultured for 0, 3, 6, 12, and 24 hours were harvested, and Western analysis was performed using a H2AX antibody (Bethyl Laboratories, Inc.) and a β-actin antibody (AC-74, Sigma-Aldrich Co. LLC.).

Figure 1:
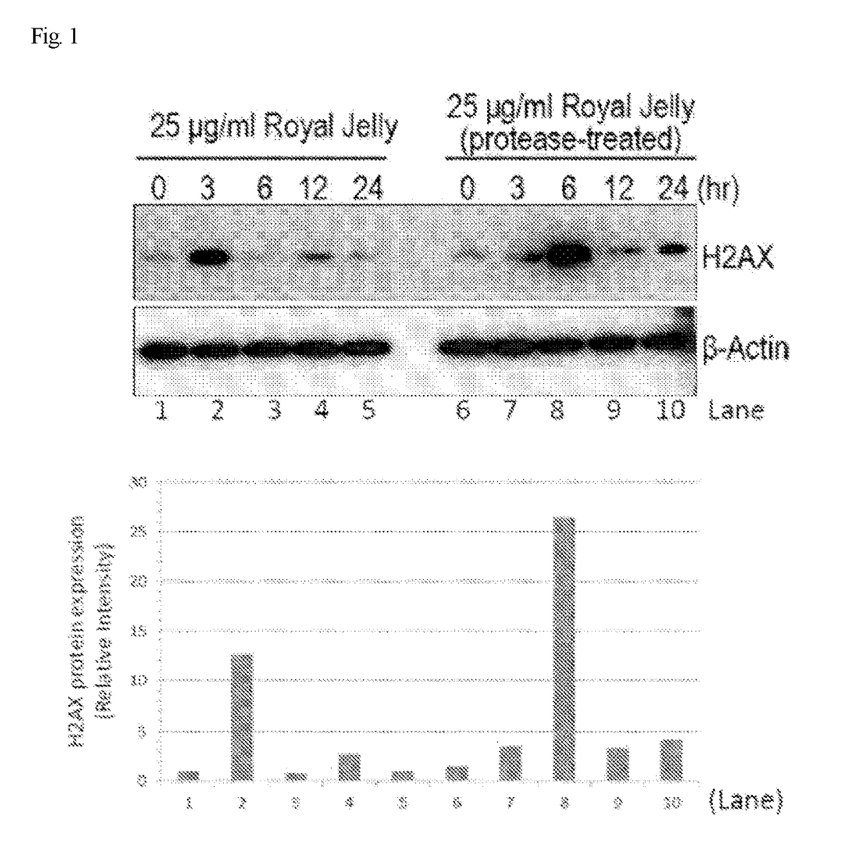
FIG. 1 shows a photograph (upper) that illustrates the results of Western analysis on H2AX expression in Test Example 1, and a graph (lower) that illustrates H2AX expression levels (relative values): left, non-treated royal jelly; right, enzyme-treated royal jelly.

FIG. 1 shows the results of Western analysis and a graph of the results of Western analysis quantified using ImageJ (Rasband, W. S., ImageJ, U. S. National Institutes of Health, Bethesda, Md., USA, http://imagej.nih.gov/ij/, 1997-2016). Induced transient H2AX expression was observed in both enzyme-treated RJ and non-treated RJ. In comparison, the H2AX expression level in lane 8 was 2.1 times that in lane 2. This result indicates that enzyme-treated RJ has a transient H2AX expression-inducing capacity 2.1 times higher than non-treated RJ.

Test Example 2

In the same manner as in Test Example 1, the effects of melinjo and trans-resveratrol on H2AX expression were analyzed. In this test example, a 0.26, 0.52, 1.0, or 2.1 w/v % melinjo seed extract or trans-resveratrol was added to a medium, and cells were cultured for 1 hour and harvested.

Figure 2:
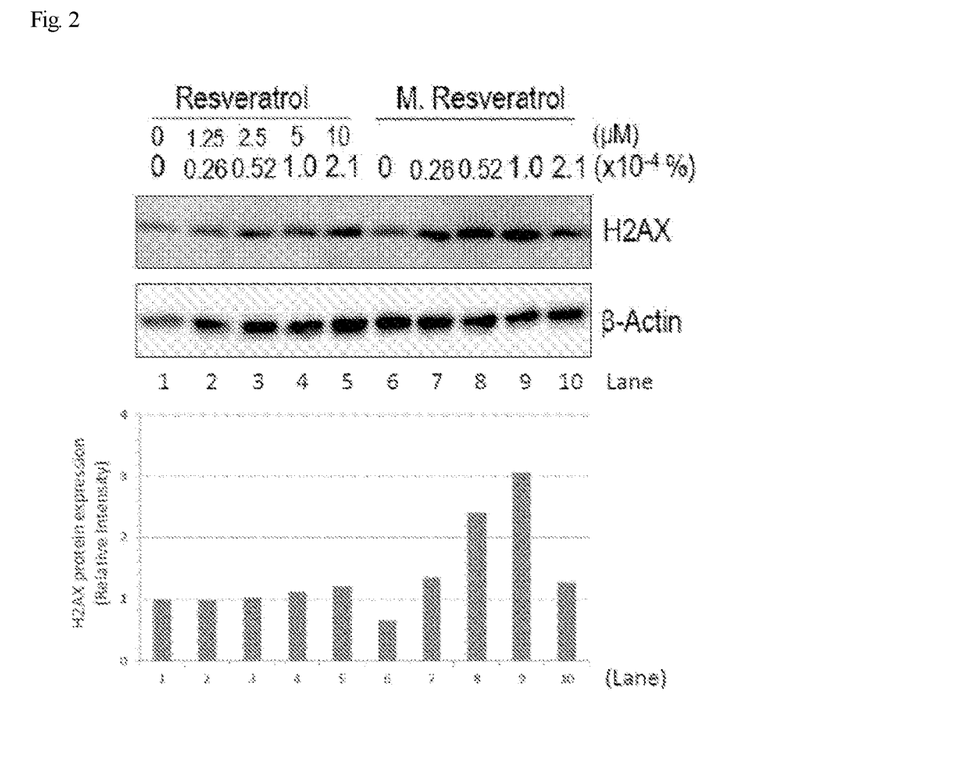
FIG. 2 shows a photograph (upper) that illustrates the results of Western analysis on H2AX expression in Test Example 2, and a graph (lower) that illustrates H2AX expression levels (relative values): left, trans-resveratrol; right, melinjo.

FIG. 2 shows the results of Western analysis and a graph of quantified results of Western analysis. Induced transient H2AX expression was observed in both melinjo and trans-resveratrol. The H2AX expression level in lane 9 was 2.7 times higher than that in lane 4. This result indicates that melinjo has a transient H2AX expression-inducing capacity 2.7 times higher than trans-resveratrol.

Test Example 3

In the same manner as in Test Example 1, the effects of trans-resveratrol, melinjo, and gnetin C on H2AX expression were analyzed. In this test example, 2.5 μM (0.52 μg/ml) of trans-resveratrol, a 0.52 μg/ml melinjo seed extract, or 2.5 μM of gnetin C was added to a medium, and cells were cultured for 0, 1.5, 3, 6, 12, and 24 hours and harvested.

Figure 3:
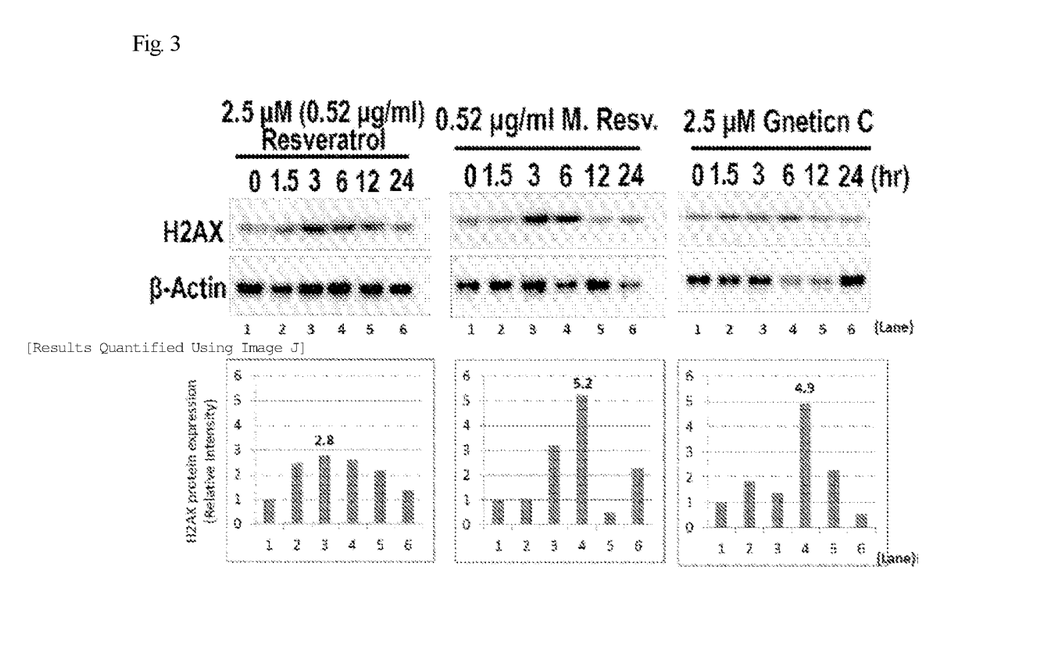
FIG. 3 shows photographs (upper) that illustrate the results of Western analysis on H2AX expression in Test Example 3, and graphs (lower) that illustrate H2AX expression levels (relative values): left, trans-resveratrol; middle, melinjo; right, gnetin C.

FIG. 3 shows the results of Western analysis and a graph of the results of Western analysis quantified using ImageJ (Rasband, W. S., ImageJ, U. S. National Institutes of Health, Bethesda, Md., USA, http://imagej.nih.gov/ij/, 1997-2016). Induced transient H2AX expression was observed in resveratrol, melinjo, and gnetin C. The H2AX expression level in Melinjo (lane 4) and gnetin C (lane 4) was respectively 1.9 times and 1.8 times higher than that of trans-resveratrol (lane 3). This result indicates that melinjo and gnetin C respectively have a transient H2AX expression-inducing capacity 1.9 times and 1.8 times higher than trans-resveratrol.

Test Example 4

To examine the genome stability enhancement effect due to melinjo in vivo, an experiment was performed on mismatch repair factor-deleted Msh2-KO mice (Lynch syndrome models that develop microsatellite instability (MSI), which is one type of genome instability). This type of mice is known to result in death between about 10 months and about 16 months of age.

Figure 4:
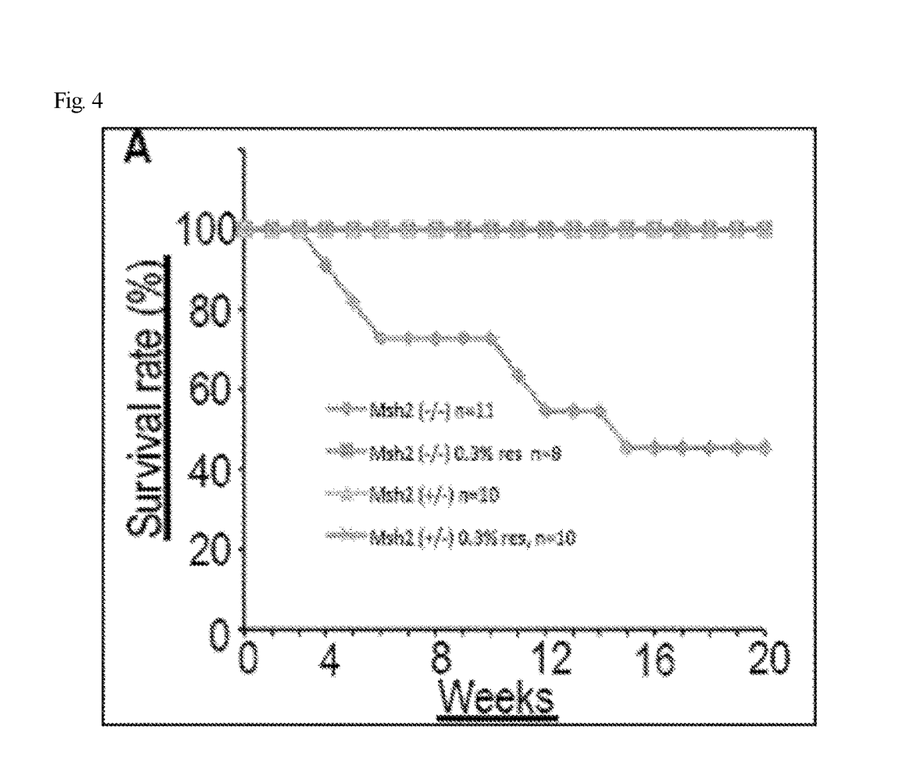
FIG. 4 shows a graph of the survival rate of Msh2 homo- and hetero-knockout mice in Test Example 4: ♦: Msh2(−/−), on a normal diet, n=11, ■: Msh2(−/−), on a diet containing a 0.3% melinjo seed extract, n=8, ▲: Msh2(+/−), on a normal diet, n=10, X: Msh2(+/−), on a diet containing a 0.3% melinjo seed extract, n=10.

FIG. 4 shows the results. A group to which 0.3 mass % (360 mg/kg body weight/day) of a melinjo seed extract, which has a transient H2AX expression-inducing capacity, was administered (■) and a group on a normal diet (♦) were compared. The results reveal that while more than half of the mice in the group on a normal diet died by 20 weeks, no mouse died during this period in the group on a diet containing a melinjo seed extract The results clearly indicate that when the gene-repair mechanism is lowered, a genome stability enhancer that has transient H2AX expression-inducing activity brings about a life extension effect.

Test Example 5

Whether the intake of melinjo has a preventive effect was examined. Water containing potassium bromate (0.02%), which is a carcinogenic agent, was administered as drinking water to a group of 8- to 12-week-old Msh2-KO mice to which a 0.03 w/v % melinjo seed extract was administered (36 mg/kg body weight/day), and a control group of mice to which sterile water was administered. After 24 weeks, the number of tumors formed in their intestinal canal was counted, and the melinjo group and the control group were compared. Mismatch repair factor-deleted Msh2-KO mice are prone to genome instability, and BrKO$_3$, which is a chemical carcinogen, easily forms tumors in the alimentary tract.

Figure 5:
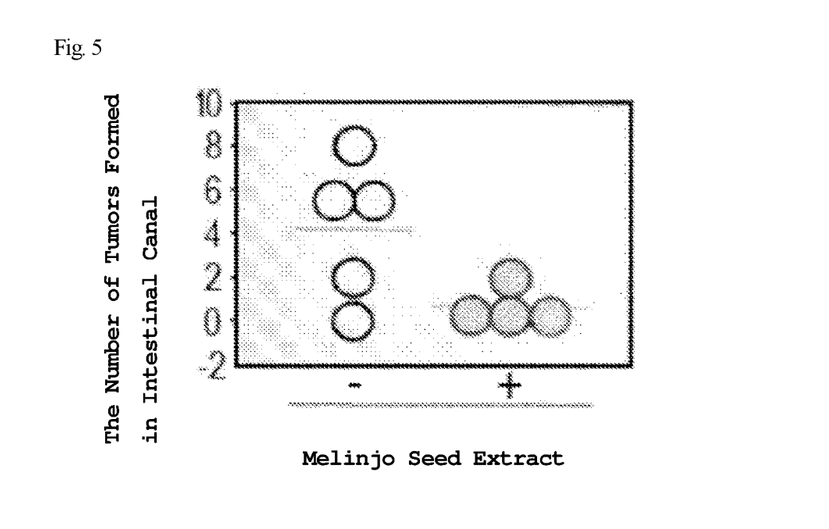
FIG. 5 shows a graph that illustrates the number of tumors formed in the intestinal canal of Msh2 knockout mice in Test Example 5: +: a group to which a melinjo seed extract was administered, −: a control group.

FIG. 5 shows the results. The group to which a melinjo seed extract was administered exhibited a clear inhibiting effect on oncogenic levels. This indicates that those predisposed to genome instability can prevent the development of cancer by taking a melinjo seed extract prophylactically.

The invention claimed is:

1. A method for enhancing genome stability, comprising the step of administering an effective amount of at least one member selected from the group consisting of enzyme-treated royal jelly, gnetum or its extract, and gnetin C to a mammal in need thereof.

2. The method according to claim 1, wherein an effective amount of enzyme-treated royal jelly is administered.

3. The method according to claim 1, wherein an effective amount of gnetum or its extract is administered.

4. The method according to claim 1, wherein an effective amount of gnetin C is administered.

5. The method according to claim 1, wherein the enzyme-treated royal jelly is a royal jelly treated with peptidase.

6. The method according to claim 1, wherein at least one member selected from the group consisting of enzyme-treated royal jelly, gnetum or its extract, and gnetin C is administered in the form of a cosmetic.

7. The method according to claim 1, wherein at least one member selected from the group consisting of enzyme-treated royal jelly, gnetum or its extract, and gnetin C is administered in the form of a food or beverage.

8. The method according to claim 1, wherein at least one member selected from the group consisting of enzyme-treated royal jelly, gnetum or its extract, and gnetin C is administered in the form of a drug or quasi-drug.

* * * * *